(12) United States Patent
Himmler et al.

(10) Patent No.: US 7,511,153 B2
(45) Date of Patent: Mar. 31, 2009

(54) 4-ALKOXY CYCLOHEXANE-1 AMINO CARBOXYLIC ACID ESTERS AND METHOD FOR THE PRODUCTION THEREOF

(75) Inventors: Thomas Himmler, Odenthal (DE);
Reiner Fischer, Monheim (DE); Bernd Gallenkamp, Wuppertal (DE);
Hans-Joachim Knops, Monheim (DE);
Lubbertus Mulder, Hagen (DE)

(73) Assignee: Bayer CropScience AG, Monheim (DE)

( * ) Notice: Subject to any disclaimer, the term of this patent is extended or adjusted under 35 U.S.C. 154(b) by 0 days.

(21) Appl. No.: 11/589,366

(22) Filed: Oct. 30, 2006

(65) Prior Publication Data

US 2007/0043219 A1 Feb. 22, 2007

Related U.S. Application Data

(62) Division of application No. 10/332,209, filed as application No. PCT/EP01/07115 on Jun. 22, 2001, now Pat. No. 7,148,377.

(30) Foreign Application Priority Data

Jul. 5, 2000 (DE) .................... 100 32 587

(51) Int. Cl.
C07D 487/20 (2006.01)
(52) U.S. Cl. .................................. 548/300.7
(58) Field of Classification Search .............. 548/300.7; 560/125
See application file for complete search history.

(56) References Cited

U.S. PATENT DOCUMENTS

| | | | |
|---|---|---|---|
| 5,462,913 A | 10/1995 | Fischer et al. | 504/138 |
| 5,622,917 A | 4/1997 | Fischer et al. | 504/283 |
| 5,677,449 A | 10/1997 | Fischer et al. | 544/165 |
| 5,808,146 A * | 9/1998 | Goodman et al. | 562/504 |
| 5,830,826 A | 11/1998 | Fischer et al. | 504/195 |
| 5,847,211 A | 12/1998 | Fischer et al. | 564/123 |
| 5,994,274 A | 11/1999 | Fischer et al. | 504/282 |
| 6,110,872 A | 8/2000 | Lieb et al. | 504/284 |
| 6,140,358 A | 10/2000 | Lieb et al. | 514/425 |
| 6,172,255 B1 | 1/2001 | Fischer et al. | 560/24 |
| 6,251,830 B1 | 6/2001 | Fischer et al. | 504/251 |
| 6,271,180 B2 | 8/2001 | Lieb et al. | 504/292 |
| 6,316,486 B1 | 11/2001 | Lieb et al. | 514/411 |
| 6,358,887 B1 | 3/2002 | Fischer et al. | 504/284 |
| 6,380,246 B1 | 4/2002 | Lieb et al. | 514/462 |
| 6,388,123 B1 | 5/2002 | Lieb et al. | 560/76 |
| 6,469,196 B2 | 10/2002 | Fischer et al. | 560/105 |
| 6,472,419 B1 | 10/2002 | Fischer et al. | 514/425 |
| 6,486,343 B1 | 11/2002 | Lieb et al. | 560/39 |
| 6,511,942 B1 | 1/2003 | Lieb et al. | 504/299 |
| 2001/0004629 A1 | 6/2001 | Lieb et al. | 504/292 |
| 2002/0022575 A1 | 2/2002 | Fischer et al. | 504/221 |

FOREIGN PATENT DOCUMENTS

| | | |
|---|---|---|
| WO | 97/17092 | 5/1997 |
| WO | 98/05638 | 2/1998 |

OTHER PUBLICATIONS

Database CA 'Online!, Chemical Abstracts Service, Columbus, OH, US; XP002180224, Database Accession No. 80:3169, Retrieved from STN, Y. Maki, et al, "1-Amino-4-Hydroxylcyclohexane-1-Carboxylic Acid", Zusammenflasung & JP 48 067254 A (Y. Make et al, Sep. 13, 1873.
Journal of the Chemical Society, Chemical Society, Letchworth, GB, Bd. 190, 1961, Seiten 4372-4379, XP000938987 in der Anmeldung erwähnt das ganze Dokunment, L. Munday, "Amino-Acids of the Cyclohexane Series. Part I".
Canadian Journal of Chemistry, National Research Council, Ottawa, CA, Bd. 53, 1975, Seiten 3339-3350, XP000925895, ISSN: 0008-4042 in der Anmeldung erwähnt das ganze Dokument, J. T. Edward et al, "Stereochemistry of the Bucherer-Bergs and Strecker Reactions of 4-Tert-Butylcyclohexanone".
J. Org. Chem., 53, (month unavailable) 1988, pp. 4069-4074, E. W. Logusch et al, "Synthesis of α- and γ- Alkyl-Substituted Phosphinothricins: Potent New Inhibitors of Glutamine Synthetase".
Chemical & Pharmaceutical Bulletin, vol. 21, No. 4, Apr. 1973, pp. 685-691, Y. Maki et al, "Studies of Alicyclic α-Amino Acids. II.[1]) Synthesis and Unequivocal Assignment of Stereochemistry of 1-Amino-*trans*- and *cis*-4-hydroxycyclohexane-1-carboxylic Acids".
Chem. Pharm. Bull., 21, (month unavailable), 1973, pp. 2460-2465, Y. Maki, et al, "Studies of Alicyclic α-Amino Acids. III.[1]) Synthesis and Biological Evaluation of 3-Amino=1,2,3,4-tetrahydrocarbazole-3-carboxylic Acids[2]".
Can. J. Chem., 53, (month unavailable) 1975, pp. 339-3350, J. T. Edward et al, "Stereochemistry of the Bucherer-Bergs and Strecker Reactions of 4-*tert*-Butylcyclohexanone".

(Continued)

Primary Examiner—Taylor Victor Oh
(74) Attorney, Agent, or Firm—Raymond J. Harmuth; Richard E. L. Henderson

(57) ABSTRACT

The invention relates to novel 4-alkoxy-cyclohexane-1-amino-carboxylic esters of the formula (IV)

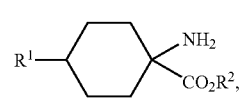

(IV)

in which $R^1$ and $R^2$ are as defined in the description,
to intermediates and processes for their preparation and to their use as intermediates in the synthesis of insecticidal, acaricidal and herbicidal compounds or pharmaceutically active compounds.

6 Claims, No Drawings

OTHER PUBLICATIONS

Can. J. Chem., 57, (month unavailable) 1979, pp. 1456-1461, G. G. Trigo et al, "Stereochemistry of the Bucherer-Bergs and Strecker Reactions of tropinone, cis-bicyclo[3.3.0]octan-3-one and cis-3,4-dimethylcyclopentanone".

J. Heterocycl. Chem., 21, (month unavailable), 1984, pp. 1527-1531, C. Pedregal et al, "Utilisation des plans factoriels fractionnaires pour l'étude de la réaction de Bucherer-Bergs: synthése de la cyclohexane spirohydantoïne".

Helvetica Chimica Acta, vol. 67 (month unavailable) 1984, pp. 1291-1297, Carmen del Campo et al, "1.45 Synthése facile de dérivés du diphényl-2,4-aza-3-bicyclo[ 3.3.1]nonane et du diphényl-7,9-aza-8-bicyclo[4.3.1]décane[1])".

* cited by examiner

4-ALKOXY CYCLOHEXANE-1 AMINO CARBOXYLIC ACID ESTERS AND METHOD FOR THE PRODUCTION THEREOF

This is a divisional application of U.S. patent application Ser. No. 10/332,209 filed Jan. 3, 2003, now U.S. Pat. No. 7,148,377 issued Dec. 12, 2006, which in turn was the national stage of PCT Application Ser. No. PCT/EP01/07115 filed Jun. 22, 2001, which in turn claimed priority of German Patent Application No. 100 32 587 filed Jul. 5, 2000.

The invention relates to novel 4-alkoxy-cyclohexane-1-amino-carboxylic esters, to intermediates and processes for their preparation and to their use as intermediates in the synthesis of insecticidal, acaricidal and herbicidal compounds or pharmaceutically active compounds.

Substituted cyclic aminocarboxylic acids can generally be obtained by the Bucherer-Bergs synthesis or by the Strecker synthesis, resulting in each case in different isomeric forms. Thus, using the conditions of the Bucherer-Bergs synthesis in the preparation of the substituted cyclic aminocarboxylic acids of the general formula (I)

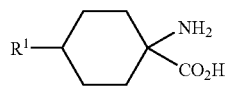
(I)

give predominantly the isomer (I-a),

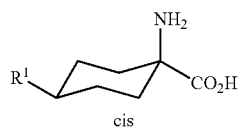
(I-a)

in which the radical $R^1$ and the amino group are arranged cis to one another, whereas the conditions of the Strecker synthesis give predominantly the trans isomer (I-b)

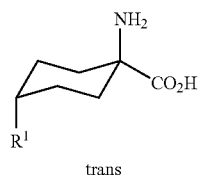
(I-b)

(J. Chem. Soc. 1961, 4372-4379; Chem. Pharm. Bull. 21 (1973) 685-691; Chem. Pharm. Bull. 21 (1973) 2460-2465; Can. J. Chem. 53 (1975) 3339-3350).

The Bucherer-Bergs reaction is generally carried out by reacting a substituted cyclic ketone of the general formula (II)

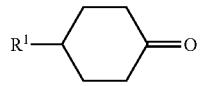
(II)

in a solvent or solvent mixture with ammonium carbonate and an alkali metal cyanide, generally sodium cyanide or potassium cyanide, followed by isolation of the resulting hydantoin of the general formula (III)

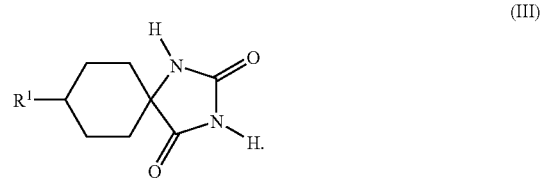
(III)

Here, the hydantoins of the general formula (III) are usually obtained as mixtures of the cis isomers (III-a)

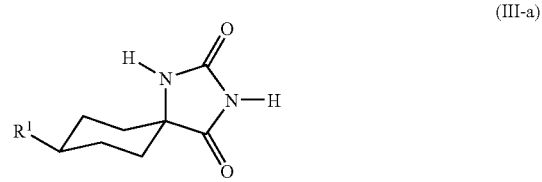
(III-a)

and trans isomers (III-b)

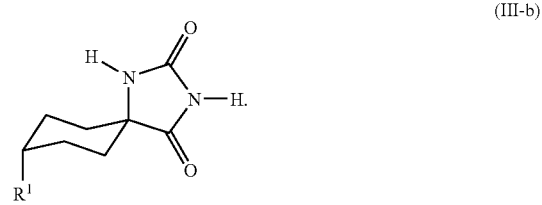
(III-b)

The hydantoins of the general formula (III) are subsequently hydrolysed by known methods, under acidic or alkaline conditions, to give the substituted cyclic aminocarboxylic acids of the general formula (I).

The substituted cyclic aminocarboxylic acids of the general formula (I) can then be esterified by known methods of organic chemistry to give the substituted cyclic aminocarboxylic esters of the general formula (IV)

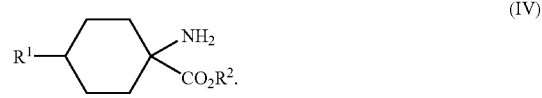
(IV)

We have found novel compounds of the formulae (IV-a) and (IV-b)

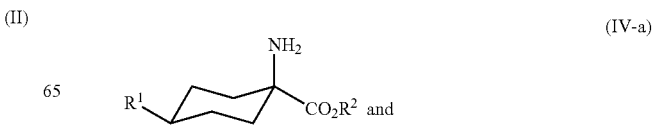
(IV-a)

-continued

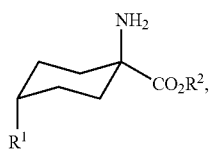
(IV-b)

in which
$R^1$ represents $OR^3$,
$R^2$ represents alkyl and
$R^3$ represents alkyl.

Preference is given to compounds of the formulae (IV-a) and (IV-b), in which
$R^1$ represents $OR^3$,
$R^2$ represents $C_1$-$C_6$-alkyl and
$R^3$ represents $C_1$-$C_4$-alkyl.

Particular preference is given to compounds of the formulae (IV-a) and (IV-b) in which
$R^1$ represents $OR^3$,
$R^2$ represents methyl, ethyl, n-propyl or n-butyl and
$R^3$ represents methyl, ethyl, n-propyl, n-butyl or i-butyl.

Some compounds (for example from EP-A-596298; WO 95/20572, EP-A-668267; WO 95/26954; WO 96/25395; WO 96/35664; WO 97/02243; WO 97/01535; WO 97/36868; WO 98/05638) require substituted cyclic aminocarboxylic esters of the general formula (IV) as precursors.

For certain of these compounds disclosed, for example, in EP-A-596298; WO 95/20572; EP-A-668267; WO 95/26954; WO 96/25395; WO 96/35664; WO 97/02243; WO 97/01535; WO 97/36868; WO 98/05638, a preparation with the use of substituted cyclic aminocarboxylic esters of the general formula (IV) in which the cis isomer (IV-a) is the only or at least the predominant isomer may be advantageous.

Solvents used for the Bucherer-Bergs reaction are, in general, approximately 50% strength aqueous methanol (J. Org. Chem. 53 (1988) 4069-4074) or approximately 50% strength aqueous ethanol (J. Chem. Soc. 1961, 4372-4379; Chem. Pharm. Bull. 21 (1973) 685-691; Chem. Pharm. Bull. 21 (1973) 2460-2465; Can. J. Chem. 53 (1975) 3339-3350; Can. J. Chem. 57 (1979) 1456-1461). In optimized Bucherer-Bergs reactions, too, the solvent used was aqueous ethanol (J. Heterocycl. Chem. 21 (1984) 1527-1531). A further solvent known for the Bucherer-Bergs reaction is N,N-dimethylformamide (Helv. Chim. Acta 67 (1984) 1291-1297). However, if these solvents are used for preparing the hydantoins of the general formula (III), unsatisfactory yields are obtained. Moreover, the isolated products are contaminated considerably by inorganic fractions. Additional purification operations result in products having compositions which vary considerably with respect to cis and trans isomers, so that a constant product quality cannot be ensured.

It has been found that compounds of the formula (III)

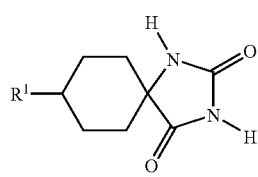
(III)

in which
$R^1$ is as defined above,
are obtained by reacting compounds of the formula (II)

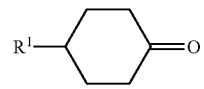
(II)

in which
$R^1$ is as defined above
with ammonium carbonate and alkali metal cyanides or trimethylsilyl cyanide (TMSCN) in the solvent water.

Surprisingly, by the process according to the invention, the compounds of the formula (III) can be obtained in high yield and purity and with a high and reproducible proportion of the cis isomer (III-a)

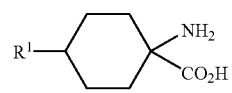
(III-a)

in which
$R^1$ represents $OR^3$, where
$R^3$ represents alkyl.

In the general formulae (II), (III) and (III-a), the radical $R^1$ represents $OR^3$, where
$R^3$ preferably represents $C_1$-$C_4$-alkyl.

Particularly preferably, $R^3$ represents methyl, ethyl, n-propyl, n-butyl or i-butyl.

Very particularly preferably, $R^3$ represents methyl.

Emphasis is given to the compound of the formula (III-a), in which $R^3$ represents methyl.

The compounds of the formula (III) and the isomers of the formulae (III-a) and (III-b) are novel and form part of the subject-matter of this invention.

In the general formula (III-b), the variable $R^1$ is as defined above.

Compounds of the formula (III) can be hydrolysed by known methods to give the compounds of the formula (I)

$$\text{(I)}$$

in which
$R^1$ is as defined above and then esterified by known methods to compounds of the formula (IV).

Preferred alkali metal cyanides which can be used for preparing the compounds of the formula (III) are lithium cyanide, sodium cyanide and potassium cyanide; particular preference is given to sodium cyanide and potassium cyanide.

Based on the ketone, the amount of alkali metal cyanide or TMSCN is from 0.9 to 3 mol per mole of ketone. Preference is given to using amounts from 1 to 2.5 mol per mole of ketone; particular preference is given to amounts from 1.1 to 2 mol of alkali metal cyanide per mole of ketone.

The amount of ammonium carbonate is from 0.5 to 7 mol of ammonium carbonate per mole of ketone. Preference is given to using amounts from 0.8 to 5 mol per mole of ketone; particular preference is given to amounts from 1 to 5 mol of ammonium carbonate per mole of ketone.

The reaction temperature for the process according to the invention is from 20 to 100° C.; preference is given to a temperature range from 30 to 70° C.

It is also possible to carry out the reaction under elevated or reduced pressure.

The reaction product is isolated in a simple manner by filtering the reaction mixture and drying the filter residue. The filtration is carried out at a temperature of from 0 to 40° C., preferably at a temperature of from 15 to 30° C.

In this manner, the desired hydantoins of the formula (III) are obtained in high yield and purity, with a reproducible isomer ratio.

The process according to the invention can be illustrated, for example, by the scheme below:

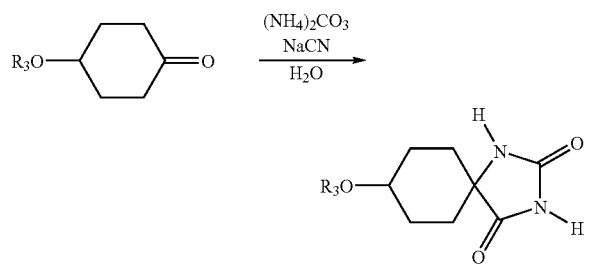

This invention also provides a process for preparing the compounds of the formula (III-a)

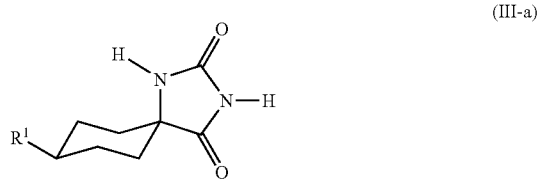

in which
R$^1$ is as defined above, characterized in that compounds of the formula (II),

in which
R$^1$ is as defined above are reacted with an alkali metal cyanide and ammonium carbonate in water.

Particular preference is given to a process for preparing the compound of the formula (III-a), in which
R$^1$ represents OR$^3$, where
R$^3$ represents methyl, characterized in that 4-methoxycyclohexanone is reacted with an alkali metal cyanide and ammonium carbonate in water.

Suitable for use as alkali metal cyanides are lithium cyanide, sodium cyanide or potassium cyanide; preference is given to sodium cyanide and potassium cyanide. Particular preference is given to sodium cyanide.

Based on the compound of the formula (II), the amount of alkali metal cyanide is from 0.9 to 3 mol per mole of the compound of the formula (II). Preference is given to amounts of from 0.9 to 2.5 mol per mole of the compound of the formula (II); particular preference is given to amounts of from 1 to 2 mol of alkali metal cyanide per mole of the compound of the formula (II).

At the same time, the amount of ammonium carbonate is from 0.8 to 2 mol of ammonium carbonate per mole of the compound of the formula (II). Preference is given to using amounts of from 1 to 1.8 mol per mole of the compound of the formula (II).

The amount of the solvent water is from 500 to 3000 ml of water per mole of the compound of the formula (II); preference is given to an amount of water of from 1000 to 2500 ml per mole of the compound of the formula (II).

The reaction temperature for the process according to the invention is from 20 to 100° C.; preference is given to a temperature range of from 30 to 70° C.

The reaction product is isolated in a simple manner by filtering the reaction mixture and drying the filter residue. The filtration is carried out at a temperature of from 0 to 40° C., preferably at a temperature of from 0 to 20° C.

This invention also provides a process for isolating the compound of the formula (III-a),

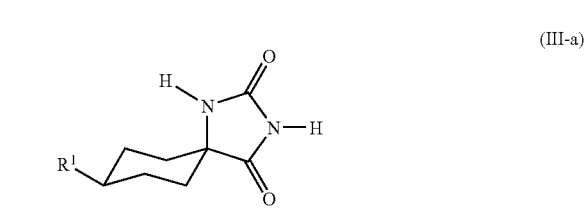

in which
R$^1$ is as defined above, characterized in that compounds of the formula (III) (cis/trans mixtures (III-a)/(III-b)) are treated with aqueous ammonia, and the solid which remains undissolved is isolated in a known manner.

Based on the trans isomer of the formula (III-b) present in the mixture, the amount of ammonia is from 1 to 30 mol per mole of the trans isomer of the formula (III-b). Preference is given to amounts of from 4 to 20 mol per mole of the trans isomer of the formula (III-b); particular preference is given to amounts of from 6 to 15 mol of ammonia per mole of the trans isomer of the formula (III-b).

The amount of the solvent water is from 500 to 3000 ml of water per mole of the compound of the formula (III); preference is given to an amount of water of from 1000 to 2500 ml per mole of the compound of the formula (III).

The temperature for the process according to the invention is from 0 to 100° C.; preference is given to a temperature range of from 10 to 60° C.

The hydantoins of the general formula (III) can be hydrolysed by known methods to the amino acids of the general formula (I), which can then be esterified by known methods to give compounds of the formula (IV).

The present invention also provides substituted cyclic aminocarboxylic acids of the general formula (I)

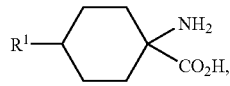
(I)

in which $R^1$ represents $OR^3$, where $R^3$ represents alky, preferably $C_1$-$C_4$-alkyl.

The substituted cyclic aminocarboxylic acids of the general formula (I) can be present either as mixtures of the cis isomers (I-a) and trans isomers (I-b), or as pure isomers.

The compounds of the formula (I) are novel and form part of the subject-matter of this invention.

Particular preference is given to compounds of the general formula (I) in which $R^1$ represents $OR^3$, where $R^3$ represents methyl or ethyl.

Very particular preference is given to compounds of the general formula (I-a), in which $R^1$ represents $OR^3$, where $R^3$ represents methyl or ethyl.

Substituted cyclic aminocarboxylic acids of the formula (I) or aminocarboxylic esters of the formula (IV) are intermediates in the preparation of other compounds which are used, for example, as active compounds in plant protection or as pharmaceutically active compounds.

Thus, for example, EP-A-596 298, WO 95/20572, EP-A-668 267, WO 95/26954, WO 96/25395, WO 96/35664, WO 97/02243, WO 97/01535, WO 97/36868, WO 98/05638 disclose that substituted cyclic aminocarboxylic acids are required for preparing substituted phenylketoenols which can be used as pesticides and herbicides.

The subject-matter of the invention is illustrated by the examples below, without limiting it in any way.

PREPARATION EXAMPLES

Comparative Example 1

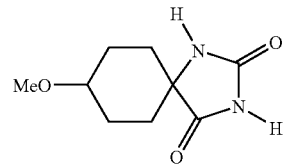

26.9 g [280 mmol] of ammonium carbonate and 5.88 g [120 mmol] of sodium cyanide are initially charged in 110 ml of water. Starting at room temperature, a solution of 7.7 g [60 mmol] of 4-methoxy-cyclohexanone in 110 ml of ethanol is added dropwise. The reaction mixture is stirred at 55-60° C. for 16 hours and then concentrated completely (according to HPLC, the cis/trans ratio is 66:34). The crude product is stirred with 100 ml of 50% strength aqueous ethanol for 1 hour, cooled to 0-5° C., stirred at 0-5° C. for 1 hour and filtered. The filter residue is dried, giving 12.07 g of a solid having a product content of 57.8% (HPLC, compared to standard), resulting in a yield of 58.7% of theory; the cis/trans ratio is 91:9. Elemental analysis shows a sodium content of 16%.

Comparative Example 2

The procedure of Comparative Example 1 was repeated. Following work-up, a product having a cis/trans ratio of 80:20 was obtained.

Example 1

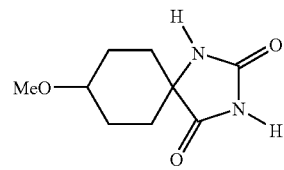

134.6 g [1.4 mol] of ammonium carbonate and 29.4 g [0.6 mol] of sodium cyanide are initially charged in 560 ml of water. Starting at room temperature, 38.5 g [0.3 mol] of 4-methoxy-cyclohexanone are added dropwise. The reaction mixture is stirred at 55-60° C. for 16 hours, cooled to 0-5° C. and stirred at this temperature for 2 hours. The solid is filtered off with suction and dried. This gives 57.88 g of a solid having a product content of 93.4% (HPLC, compared to standard), resulting in a yield of 90.9% of theory; the cis/trans ratio is 71:29. Elemental analysis shows a sodium content of 1.2%.

Example 2

134.6 g [1.4 mol] of ammonium carbonate and 22.05 g [0.45 mol] of sodium cyanide are initially charged in 560 ml of water. Starting at room temperature, 38.5 g [0.3 mol] of 4-methoxy-cyclohexanone are added dropwise. The reaction mixture is stirred at 55-60° C. for 4 hours, cooled to 0-5° C.

and stirred at this temperature for 2 hours. The solid is filtered off with suction and dried. This gives 57.64 g of a solid having a product content of 93.7% (HPLC, compared to standard), resulting in a yield of 90.8% of theory; the cis/trans ratio is 72:28. Elemental analysis shows a sodium content of 1.3%.

Example 3

134.6 g [1.4 mol] of ammonium carbonate and 16.17 g [0.33 mol] of sodium cyanide are initially charged in 560 ml of water. Starting at room temperature, 38.5 g [0.3 mol] of 4-methoxy-cyclohexanone are added dropwise. The reaction mixture is stirred at 55-60° C. for 4 hours, cooled to 0-5° C. and stirred at this temperature for 2 hours. The solid is filtered off with suction and dried. This gives 61.02 g of a solid having a product content of 94.1% (HPLC, compared to standard), resulting in a yield of 96.5% of theory; the cis/trans ratio is 71:29.

Example 4

The procedure of Example 3 is repeated. This gives 59.54 g of a solid having a pro-duct content of 93.6% (HPLC, compared to standard), resulting in a yield of 93.7% of theory; the cis/trans ratio is 71:29.

Example 5

134.6 g [1.4 mol] of ammonium carbonate and 16.17 g [0.33 mol] of sodium cyanide are initially charged in 560 ml of water. Starting at room temperature, 38.5 g [0.3 mol] of 4-methoxy-cyclohexanone are added dropwise. The reaction mixture is stirred at 55-60° C. for 4 hours and then stirred at room temperature overnight. At room temperature the solid is filtered off with suction and dried. This gives 58.5 g of a solid having a product content of 95.4% (HPLC, compared to standard), resulting in a yield of 93.9% of theory; the cis/trans ratio is 71:29.

Example 6

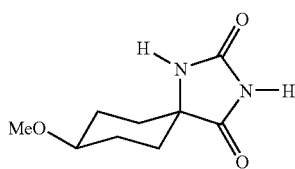

43.2 g [0.45 mol] of ammonium carbonate and 29.4 g [0.6 mol] of sodium cyanide are initially charged in 560 ml of water. Starting at room temperature, 38.5 g [0.3 mol] of 4-methoxy-cyclohexanone are added dropwise. The reaction mixture is stirred at 55-60° C. for 4 hours, cooled to 0-5° C. and stirred at this temperature for 2 hours. The solid is filtered off with suction and dried. This gives 26.4 g of a solid, resulting in a yield of 44.4% of theory; the cis/trans ratio is >99.7:0.3.

Melting point: 267-268° C. (sublimation). $^1$H-NMR (400 MHz, d-DMSO): δ=1.38-1.48 (m; 2H), 1.57-1.68 (m; 4H), 1.91-1.95 (m; 2H), 3.14-3.17 (m; 1H), 3.23 (s; 3H), 8.37 (s; 1H) ppm.

Example 7

34.6 g [0.36 mol] of ammonium carbonate and 29.4 g [0.6 mol] of sodium cyanide are initially charged in 560 ml of water. Starting at room temperature, 38.5 g [0.3 mol] of 4-methoxy-cyclohexanone are added dropwise. The reaction mixture is stirred at 55-60° C. for 4 hours, cooled to 0-5° C. and stirred at this temperature for 2 hours. The solid is filtered off with suction and dried. This gives 18.8 g of a solid, resulting in a yield of 31.6% of theory; the cis/trans ratio is 99.4:0.6.

Example 8

28.8 g [0.3 mol] of ammonium carbonate and 16.2 g [0.33 mol] of sodium cyanide are initially charged in 560 ml of water. Starting at room temperature, 38.5 g [0.3 mol] of 4-methoxy-cyclohexanone are added dropwise. The reaction mixture is stirred at 55-60° C. for 4 hours, cooled to 0-5° C. and stirred at this temperature for 2 hours. The solid is filtered off with suction and dried. This gives 15.5 g of a solid, resulting in a yield of 26.1% of theory; the cis/trans ratio is 99.2:0.8.

Example 9

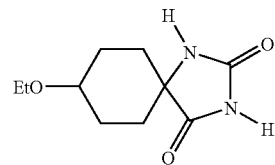

13.5 g [140 mmol] of ammonium carbonate and 1.62 g [33 mmol] of sodium cyanide are initially charged in 56 ml of water. Starting at room temperature, 4.3 g [30 mmol] of 4-ethoxy-cyclohexanone are added dropwise. The reaction mixture is stirred at 55-60° C. for 4 hours, cooled to 0-5° C. and stirred at this temperature for 2 hours. The solid is filtered off with suction and dried. This gives 5.55 g of a solid (78.8% of theory); the cis/trans ratio is 72:28.

$^1$H-NMR (400 MHz, d-DMSO): δ=1.09 (t; 3H, cis), 1.12 (t; 3H, trans), 1.3-1.48 (m; 2H, cis+trans), 1.57-1.64 (m; 4H, cis+trans), 1.77-1.95 (m; 2H, cis+trans), 3.25-3.3 (m; 1H, cis+trans), 3.40 (q; 2H, trans), 3.45 (q; 2H, cis), 8.40 (s, br; 1H, cis+trans) ppm.

Further examples of the formula (III)

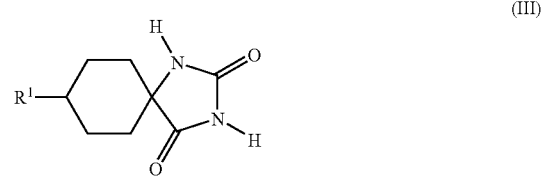

(III)

which may be mentioned are:

Example 10

R$^1$=O—$^n$C$_3$H$_7$ m.p.>250° C. cis/trans=87/13

Example 11

R$^1$=O—$^n$C$_4$H$_9$ m.p.>250° C. cis/trans=85/15

Example 12

R$^1$=O—$^i$C$_4$H$_9$ m.p.>250° C. cis/trans=51/49

Example 13

In an autoclave, 19.8 g [0.1 mol] of 4-methoxycyclohexane-1-spiro-5'-hydantoin (cis/trans ratio 71:29), 4 g [0.1 mol] of sodium hydroxide and 400 ml of water are heated at 160° C. for 24 hours. With ice-cooling, the reaction mixture is adjusted to pH 3 using hydrochloric acid and concentrated substantially under reduced pressure. The remaining water is removed by azeotropic distillation with toluene. This gives 29.6 g of a solid.

According to GC/MS (after silylation), 3.7% of starting material and 89.3% of 4-methoxycyclohexane-1-amino-carboxylic acid are present; the cis/trans ratio is 70:30.

GC/MS(sil.): m/e=302 (product (disilylated)-15), 200 (base peak, product (disilylated)-CO$_2$SiMe$_3$), 168 (200-MeOH).

Example 14

In an autoclave, 7.9 g [40 mmol] of cis-4-methoxycyclohexane-1-spiro-5'-hydantoin, 160 ml of water and 1.6 g [40 mmol] of sodium hydroxide are heated at 160° C. for 24 hours. With ice-cooling, the reaction mixture is adjusted to pH 3 using hydrochloric acid and substantially concentrated under reduced pressure. The remaining water is removed by azeotropic distillation with toluene. This gives 11.2 g of a solid.

m.p.>400° C. $^1$H-NMR (400 MHz, d$_6$-DMSO): δ=3.17 (m, 1H, C$\underline{H}$OCH$_3$), 3.22 (s, 3H, OC$\underline{H}_3$) ppm.

Example 15

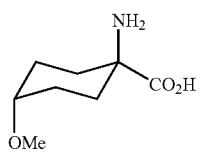

In an autoclave, 1 g [5 mmol] of trans-4-methoxycyclohexane-1-spiro-5'-hydantoin, 20 ml of water and 0.2 g [5 mmol] of sodium hydroxide are heated at 160° C. for 24 hours. With ice-cooling, the reaction mixture is adjusted to pH 3 using hydrochloric acid and substantially concentrated under reduced pressure. The remaining water is removed by azeotropic distillation with toluene.

This gives 0.8 g of a solid.

Example 16

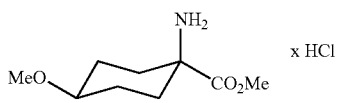

6.9 g [40 mmol] of cis-4-methoxycyclohexane-1-aminocarboxylic acid are suspended in 50 ml of anhydrous methanol. The mixture is briefly heated to reflux and then cooled to 0° C. At 0-5° C., 6.9 g [58 mmol] of thionyl chloride are added dropwise. The mixture is stirred at 0-5° C. for half an hour, then allowed to warm to room temperature, heated to 40° C. and stirred at 40° C. overnight. The reaction mixture is filtered, the filter residue is washed with 20 ml of methanol and the filtrate is concentrated. The residue is stirred with 50 ml of methyl tert-butyl ether and filtered off with suction, and the residue is dried. This gives 5.6 g of methyl cis-4-methoxy-cyclohexane-1-aminocarboxylate hydrochloride (63% of theory).

m.p. 298° C. $^1$H-NMR (400 MHz, d-DMSO): δ=1.64-1.80 (m; 4H), 1.88-1.96 (m; 4H), 3.23 (s; 3H), 3.29-3.32 (m; 1H), 3.76 (s; 3H), 8.67 (s, br; 3H) ppm.

Example 17

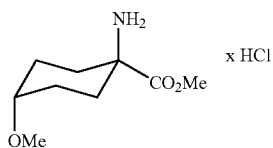

In the same manner as described in Example 12, methyl trans-4-methoxycyclohexane-1-aminocarboxylate hydrochloride is prepared.

m.p. 173° C. $^1$H-NMR (400 MHz, d$_6$-DMSO): δ=185-2.37 (4 m, 8H, CH$_2$), 3.32 (s, 3H, CHOC$\underline{H}_3$), 3.50 ("d", 1H, C$\underline{H}$OCH$_3$), 3.82 (s, 3H, OC$\underline{H}_3$), 8.94 (br, 3H, $^\oplus$NH$_3$) ppm.

Similarly to Example 15, the following amino acid esters of the formula (IV) are obtained

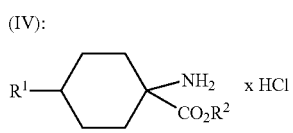

Example 18

R$^1$=O—C$_2$H$_5$ R$^2$=Me m.p.>220° C.

Example 19

R$^1$=O—$^n$C$_3$H$_7$ R$^2$=Me m.p.>220° C.

Example 20

R¹=O—$^n$C₄H₉ R²=Me m.p. 183° C.

Example 21

R¹=O—$^i$C₄H₉ R²=Me m.p. 179° C.

Example 22

R¹=OMe R²=Et MS(silyl.): m/e=273 (M⁺)

Example 23

R¹=OMe R²=$^n$Bu ¹H-NMR ¹H-NMR (400 MHz, d-DMSO): δ=0.88-0.92 (t; 3H), 1.32-1.41 (m; 2H), 1.57-1.68 (m; 2H), 1.69-2.1 (m; 10H), 3.23 (s; 3H), 3.27-3.31 (m; 1H), 4.14-4.18 (m; 2H), 8.77 (s, br; 3H) ppm.

Example 24

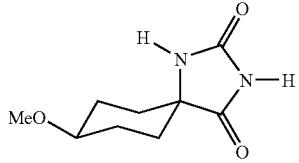

10.2 g of the compound of the formula (III) where R¹=OR³, R³ being methyl (8-methoxy-1,3-diazaspiro[4.5]decane-2,4-dione; 97% pure, cis/trans ratio=75:25) are stirred at 55° C. in 86 ml of water and 9.8 g of 26% strength ammonia for 4 hours. The mixture is cooled to 0-5° C. and stirred at this temperature for 2 hours. The solid is filtered off with suction and dried. This gives 5.37 g of a solid; the cis/trans ratio is 98.3:1.7.

Example 25

Example 24 is repeated, except that the mixture is stirred at room temperature for 4 hours. This gives 5.03 g of a solid having a cis/trans ratio of 97.7:2.3.

Example 26

10.2 g of the compound of the formula (III) where R¹=OR³, R³ being methyl (8-methoxy-1,3-diazaspiro[4.5]decane-2,4-dione; 97% pure, cis/trans ratio=75:25) are stirred at 55° C. in 86 ml of water and 6.5 g of 26% strength ammonia for 4 hours. The mixture is cooled to 0-5° C. and stirred at this temperature for 2 hours. The solid is filtered off with suction and dried. This gives 5.73 g of a solid; the cis/trans ratio is 97.3:2.7.

Example 27

10.4 g of the compound of the formula (III) where R¹=OR³, R³ being methyl (8-methoxy-1,3-diazaspiro[4.5]decane-2,4-dione; 95.3% pure, cis/trans ratio=98.2:1.8) are stirred at 55° C. in 17 ml of water and 0.69 g of 26% strength ammonia for 4 hours. The mixture is cooled to 0-5° C. and stirred at this temperature for 2 hours. The solid is filtered off with suction and dried. This gives 9.58 g of a solid; the cis/trans ratio is >99.7:0.3.

The invention claimed is:

1. Compounds of the formula (III)

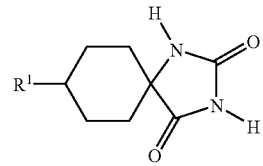

(III)

in which
R¹ represents OR³, and
R³ represents alkyl.

2. Compounds of the formula (III-a)

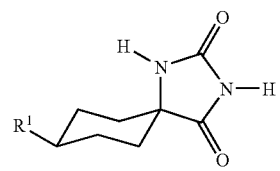

(III-a)

in which
R¹ is as defined in claim 1 above.

3. Compounds of the formula (III-b)

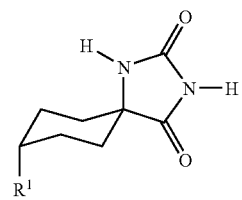

(III-b)

in which
R¹ is as defined in claim 1 above.

4. Process for preparing compounds of the formula (III),

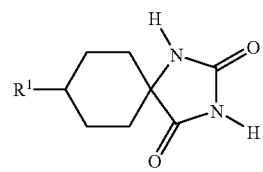

(III)

in which
R¹ is as defined in claim 1 above,
characterized in that compounds of the formula (II)

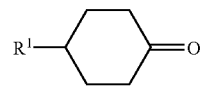

(II)

in which

R$^1$ is as defined in claim 1 above are reacted with ammonium carbonate and alkali metal cyanides or trimethylsilyl cyanide (TMSCN) in the solvent water.

5. Process for preparing compounds of the formula (III-a),

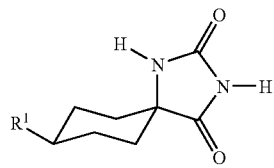
(III-a)

in which

R$^1$ is as defined in claim 1 above, characterized in that compounds of the formula (II)

(II)

in which

R$^1$ is as defined in claim 4 above are reacted with an alkali metal cyanide and ammonium carbonate in water.

6. Process for isolating compounds of the formula (III-a)

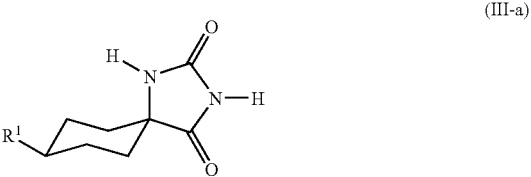
(III-a)

in which

R$^1$ is as defined in claim 1 above, characterized in that compounds of the formula (III)

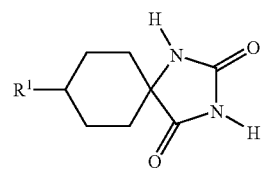
(III)

in which

R$^1$ is as defined in claim 1 above, are treated with aqueous ammonia.

* * * * *